United States Patent [19]

Hardy et al.

[11] Patent Number: 4,945,052

[45] Date of Patent: Jul. 31, 1990

[54] PRODUCTION OF A VITAMIN C PRECURSOR USING GENETICALLY MODIFIED ORGANISMS

[75] Inventors: Kimber Hardy, Geneva, Switzerland; Hendrick van de Pol, Gif Sur Yvette, France; June Grindley, Alameda, Calif.; Mark A. Payton, Geneva, Switzerland

[73] Assignee: Biogen, Inc., Cambridge, Mass.

[21] Appl. No.: 45,859

[22] PCT Filed: Aug. 1, 1986

[86] PCT No.: PCT/US86/01571

§ 371 Date: Jun. 2, 1987

§ 102(e) Date: Jun. 2, 1987

[87] PCT Pub. No.: WO87/00863

PCT Pub. Date: Feb. 12, 1987

[30] Foreign Application Priority Data

Aug. 2, 1985 [GB] United Kingdom ............... 8519536

[51] Int. Cl.$^5$ ................ C12N 15/00; C12P 21/00; C07H 15/12

[52] U.S. Cl. ................ 435/172.3; 435/68.1; 435/69.1; 435/71.2; 435/172.1; 435/252.3; 435/320; 435/189; 536/27; 935/60; 935/61

[58] Field of Search .......... 435/123, 138, 170, 172.1, 435/172.3, 189, 320, 252.3; 935/14, 29, 38, 56, 61, 72

[56] References Cited

U.S. PATENT DOCUMENTS

| | | | |
|---|---|---|---|
| 3,922,194 | 11/1975 | Sonoyama et al. | 195/30 |
| 3,959,076 | 5/1976 | Sonoyama et al. | 195/30 |
| 3,963,574 | 6/1976 | Sonoyama et al. | 195/30 |
| 4,731,328 | 3/1988 | Maxwell | 435/253 |
| 4,757,012 | 7/1988 | Estell et al. | 435/172.3 |
| 4,758,514 | 7/1988 | Light et al. | 435/91 |

FOREIGN PATENT DOCUMENTS

| | | | |
|---|---|---|---|
| 0046284 | 2/1982 | European Pat. Off. | |
| 0088408 | 9/1983 | European Pat. Off. | |
| 0088409 | 11/1983 | European Pat. Off. | |
| 132308 | 1/1985 | European Pat. Off. | 435/172.3 |
| 0142169 | 5/1985 | European Pat. Off. | |

OTHER PUBLICATIONS

Sonoyama et al., (1982), Apl. Env. Microbiol., 43:1064–1069.
T. Sonoyama et al., "Production of 2–Keto–L–Gulonic Acid from D–Glucose by Two-Stage Fermentation," *Appl. Environ. Microbiol.*, 43, pp. 1064–1069, (1982).
Anderson et al., (1985), Science, 230:145–149.
Chemical Abstract, CA 105(3):23127, (1986), (JP 6163278, 4/1/86).

*Primary Examiner*—Richard A. Schwartz
*Assistant Examiner*—Anne R. Brown
*Attorney, Agent, or Firm*—James F. Haley, Jr.; Leon R. Yankwich; John R. Storella

[57] ABSTRACT

An enzyme for conversion of 2,5-diketo-D-gluconate (2,5-DKG) to 2-keto-L-gulonic acid (2-KLG) and a genetically modified organism that expresses all the fermentation enzymes needed to convert glucose to 2-KLG (a precursor to ascorbic acid) using the new enzyme are described. Preferably, the organism is *Erwinia citreus*, or a mutated strain of *Erwinia citreus*, unable to use 2,5-DKG or 2-KLG as a sole carbon source, into which the gene for a 2,5-DKG reductase, produced by *Corynebacterium sp.*, SHS 752001, has been inserted. The preferred transformed organism expresses the fermentation enzymes *Erwinia citreus* normally expresses for fermentation of glucose to 2,5-DKG and, in addition, an enzyme *Corynebacterium sp.* SHS 752001 expresses for fermentation of 2,5-DKG to 2-KLG.

16 Claims, 5 Drawing Sheets

FIGURE 1

| # | AA | | # | AA | |
|---|---|---|---|---|---|
| 1 | Pro | | 31 | Ala | |
| 2 | Asn | PROBE I | 32 | Ala | |
| 3 | Ile | | 33 | Met | |
| 4 | Pro | | 34 | Val | |
| 5 | Thr | | 35 | Ala | |
| 6 | Ile | | 36 | Ala | |
| 7 | Ser | | 37 | Ile | |
| 8 | Leu | | 38 | Asp | |
| 9 | Asn | | 39 | Ser | |
| 10 | Asp | | 40 | Gly | |
| 11 | Gly | | 41 | Tyr | |
| 12 | Arg | | 42 | Arg | |
| 13 | Pro | | 43 | Leu | |
| 14 | Phe | | 44 | Leu | |
| 15 | Pro | | 45 | Asp | |
| 16 | Glu | | 46 | Thr | |
| 17 | Leu | | 47 | Ala | |
| 18 | Gly | | 48 | Val | |
| 19 | Leu | | 49 | Asn | |
| 20 | Gly | | 50 | Tyr | |
| 21 | Thr | | 51 | Glu | PROBE III |
| 22 | Tyr | | 52 | Asn | |
| 23 | Asn | | 53 | Glu | |
| 24 | Leu | | 54 | Ser | |
| 25 | Leu | | 55 | Cys or Glu | |
| 26 | Gly | | 56 | Val | |
| 27 | Asp | | 57 | ? | |
| 28 | Glu | PROBE II | 58 | Arg ? | |
| 29 | Gly | | 59 | Ala | |
| 30 | Val | | 60 | Val | |

FIGURE 2

1 Leu
2 Lys
3 Thr
4 Leu
5 Ile
6 Asp
7 Glu
8 Thr
9 Gly
10 Val
11 Thr ?
12 Pro
13 Ala ?
14 Val
15 Asn
16 Ala
17 Val
18 Glu
19 Leu
20 His or Arg
21 Pro
22 Tyr
23 Phe
24 Pro     PROBE IV
25 Gln
26 Ala
27 Ala
28 Leu
29 ?
30 Ala

```
            T
5' GGPATPTTNGG              5' ACNCCTTCPTCNCC
    DNA PROBE I                 DNA PROBE II
    FIG. 3(a)                   FIG. 3(b)

5' GAQTCPTTQTCPTAPTT        5' CTQTCPTTQTCPTAPTT
    DNA PROBE III'              DNA PROBE III''
    FIG. 3(c)                   FIG. 3(d)

5' GCQTGNGGPAAPTA
    DNA PROBE IV
    FIG. 3(e)
```

FIGURE 4

```
ATGCCGAACATCCCCACCATCAGCCTCAACGACGGACGCCCCTTCGCGGAGCCTGGGCTC
MetProAsnIleProThrIleSerLeuAsnAspGlyArgProPheAlaGluProGlyLeu

GGCACGTACAACCTGCGCGGCGACGAGGGGGTCGCGGCCATGGTCGCCGCGATCGACTCG
GlyThrTyrAsnLeuArgGlyAspGluGlyValAlaAlaMetValAlaAlaIleAspSer

GGCTACCGCCTGCTCGACACGGCGGTGAACTACGAGAACGAGAGCGAGGTCGGCCGAGCG
GlyTryArgLeuLeuAspThrAlaValAsnTyrGluAsnGluSerGluValGlyArgAla

GTGCGCGCGAGCAGCGTCGATCGCGACGAGCTCATCGTGGCGAGCAAGATCCCGGGCCGC
ValArgAlaSerSerValAspArgAspGluLeuIleValAlaSerLysIleProGlyArg

CAGCACGGGCGCGCCGAGGCGGTCGACAGCATCCGCGGATCGCTCGACCGGCTGGGGCTC
GlnHisGlyArgAlaGluAlaValAspSerIleArgGlySerLeuAspArgLeuGlyLeu

GACGTGATCGACCTGCAGCTGATCCACTGGCCGAACCCCAGCGTGGGCCGGTGGCTCGAC
AspValIleAspLeuGlnLeuIleHisTrpProAsnProSerValGlyArgTrpLeuAsp

ACCTGGCGCGGCATGATCGACGCGCGCGAGGCGGGCCTGGTCCGCTCGATCGGCGTCTCG
ThrTrpArgGlyMetIleAspAlaArgGluAlaGlyLeuValArgSerIleGlyValSer

AACTTCACCGAGCCGATGCTGAAGACCCTCATCGACGAGACCGGGGTCACACCCGCGGTC
AsnPheThrGluProMetLeuLysThrLeuIleAspGluThrGlyValThrProAlaVal

AACCAGGTCGAGCTCCACCCGTACTTCCCCCAGGCGGCGCTGCGCGCGTTCCACGACGAG
AsnGlnValGluLeuHisProTyrPheProGlnAlaAlaLeuArgAlaPheHisAspGlu

CACGGCATCCGCACCGAGAGCTGGAGCCCGCTCGCCCGGCGCAGCGAGCTGCTCACCGAG
HisGlyIleArgThrGluSerTrpSerProLeuAlaArgArgSerGluLeuLeuThrGlu

CAGCTGCTGCAGGAGCTGGCGGTCGTCTACGGAGTGACGCCGACGCAGGTGGTGCTGCGG
GlnLeuLeuGlnGluLeuAlaValValTyrGlyValThrProThrGlnValValLeuArg

TGGCACGTGCAGCTCGGCAGCACCCCGATCCCCAAGTCCGCCGACCCCGATCGCCAGCGC
TrpHisValGlnLeuGlySerThrProIleProLysSerAlaAspProAspArgGlnArg

GAGAACGCCGATGTGTTCGGCTTCGCCCTCACCGCCGACCAGGTCGATGCGATCTCGGGC
GluAsnAlaAspValPheGlyPheAlaLeuThrAlaAspGlnValAspAlaIleSerGly

CTCGAGCGCGGGCGGCTCTGGGACGGCGACCCCGACACGCACGAAGAGATGTAG
LeuGluArgGlyArgLeuTrpAspGlyAspProAspThrHisGluGluMetSTOP
```

PRODUCTION OF A VITAMIN C PRECURSOR USING GENETICALLY MODIFIED ORGANISMS

TECHNICAL FIELD OF THE INVENTION

This invention relates to DNA sequences, recombinant DNA molecules, organisms containing such sequences and molecules, the expression of certain enzymes by such organisms, and the production, by fermentation, of a Vitamin C precursor using such organisms and enzymes. More specifically, this invention relates to an expression vehicle and genetically modified organisms, transformed by that vehicle, that express enzymes used to convert glucose, or another carbon source, by fermentation to 2-keto-L-gluconic acid (2-KLG), a chemical precursor to Vitamin C (ascorbic acid).

BACKGROUND ART

There are several processes for producing Vitamin C. One process involves a number of chemical synthesis steps and one fermentation step. Briefly, the steps are hydrogenation of glucose to sorbitol, fermentation of sorbitol to sorbose using *Acetobacter suboxydans*, sorbose acetonization, diacetone sorbose oxidation to 2-KLG, esterification of 2-KLG, and conversion of the ester to ascorbic acid. This process is complex and requires a relatively high capital investment for an operating plant.

Another process involves two fermentation steps. The process starts with fermentation of glucose to 2,5-diketo-D-gluconate (2,5-DKG) by Erwinia sp.; fermentation of 2,5-DKG to 2-KLG by Corynebacterium sp.; esterification of 2-KLG; and conversion of the ester to ascorbic acid. One study has shown that D-gluconate and 2-keto-D-gluconate (2-KDG) are produced sequentially from glucose by Erwinia sp. before 2,5-DKG is produced in the first fermentation step. See T. Sonoyama et al., "Production of 2-keto-L-gulonic acid from D-glucose by Two-Stage Fermentation," *App. and Envir. Microbiol.*, 43, 1064–69 (1982). This two-step fermentation process, although having a somewhat lower capital cost than the Acetobacter process, is still complex and expensive to operate.

Still another process for converting glucose to 2-KLG is referred to in European patent application No. 132,308. That application refers to the conversion of glucose to 2-KLG in a single step fermentation process. It first refers to Corynebacterium sp. ATCC 31090 as a source of a DNA sequence coding for a particular 2,5-DKG reductase (an enzyme that is said to catalyze the fermentation of 2,5-DKG to 2-KLG). This DNA sequence, with its own or a synthetic ribosome binding site, is then said to be inserted "downstream" of an *E. coli* trp or tac promoter or the pACYC184 CAT promoter in an expression vector. The vector is also said to contain a gene coding for tetracycline resistance or other selectable marker, and an origin of replication derived from plasmids ColE1, 115A, or RSF 1010. A host cell, *Erwinia herbicola* (ATCC 21998), is then said to be transformed with the vector. On fermentation this transformed cell is said to produce 2-KLG from glucose in one step. The conversion of glucose to 2-KLG in that process, however, is not fully satisfactory because the yield of 2-KLG is very low and the time of fermentation to obtain even that low yield is too long.

Accordingly, a single organism capable of converting a carbon source, such as glucose, to 2-KLG at acceptable rates and in a single fermentation step is still a goal that has not been attained.

SUMMARY OF THE INVENTION

The present invention solves the problem of finding a single organism capable of converting glucose, or other carbon source, into 2-KLG quickly and in high yield. In one embodiment, this invention provides an expression vehicle capable of transforming a host so that it performs all of the fermentation steps required for converting glucose, or other carbon source, to 2-KLG in a single fermentation at acceptable conversion rates, without intermediate product recovery or intermediate purification steps. The 2-KLG resulting from practice of the present invention may then be esterified and converted to ascorbic acid (Vitamin C), as in the conventional processes described above.

In contrast to the process of the present invention, the known commercial fermentation processes for converting glucose to 2-KLG require two separate organisms, for example strains of Erwinia and Corynebacterium, to transform glucose to 2-KLG.

One advantage of the present invention is that a single strain of a genetically modified organism achieves significant yields of 2-KLG directly from glucose in a single fermentation. Thus, the ability of the process of this invention to use a single fermentation step results in a relatively simpler process than the known commercial process so that less process equipment and less energy is required to produce Vitamin C from glucose.

Another object of the present invention is to provide a novel 2,5 DKG reductase and a novel transformed organism superior to those referred to in European patent application No. 132,308, and the processes and products of the present invention are accordingly unexpectedly improved and patentable over the processes and products of European patent application No. 132,308.

Still other objects and aspects of the invention will be apparent from the specification.

BRIEF DESCRIPTION OF THE DRAWINGS

FIG. 1 depicts a partial amino acid sequence from the N-terminus of the 2,5-DKG reductase of this invention;

FIG. 2 depicts part of the amino acid sequence of a 14,000d molecular weight cyanogen bromide fragment of the 2,5-DKG reductase of this invention;

FIGS. 3a–e depict the sequences of several nucleotide probes used to locate by hybridization portions of the Corynebacterium genome containing the 2,5-DKG reductase gene of this invention; and FIG. 4 depicts the DNA sequence of the 2,5-DKG reductase gene of this invention and the corresponding amino acid sequence of the 2,5-DKG reductase of this invention.

In FIG. 5, the symbols have the following meanings: PL, $P_L$ promoter; S-D, Shine-Dalgarno sequence; ori, origin of replication; Lac, lac promoter; amp-r, ampicillin resistance gene.

BEST MODE OF CARRYING OUT THE INVENTION

Figure 5:
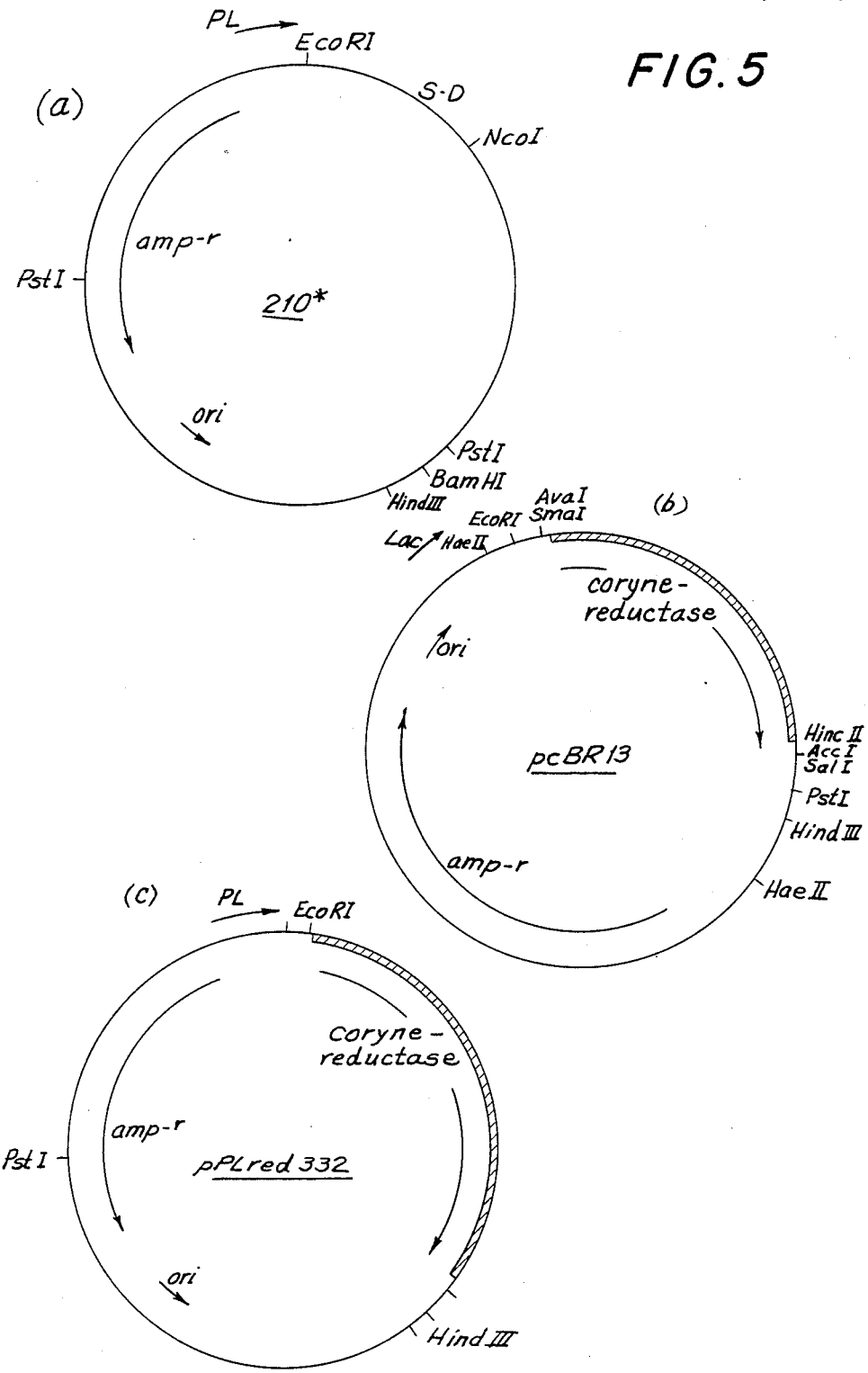
FIG. 5 depicts the construction of plasmid pPLred332 from plasmids 210* and pcBR13.

In order that the present invention may be more fully understood, the following detailed description is provided. In this specification some of the following terms are employed:

Nucleotide

A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four RNA bases are A, G, C, and uracil ("U"). For DNA, "P" indicates either of the purines (A or G), "Q" indicates either of the pyrimidines (C or T), and "N" indicates any of the four bases (A, G, C, or T). For RNA, "P," "Q," and "N" have the same meanings except that "U" is substituted for "T."

DNA Sequence

A linear array of deoxy nucleotides connected one to the other by phosphodiester bonds between the 3' and 5' carbons of adjacent pentoses.

Codon

A DNA sequence of three nucleotides (a triplet) that encodes, through its mRNA, an amino acid, a translation start signal, or a translation termination signal. For example, the nucleotide triplets TTA, TTG, CTT, CTC, CTA, and CTG encode for the amino acid leucine ("Leu"); TAG, TAA, and TGA are translation stop signals; and ATG is a translation start signal that also codes for methionine.

Reading Frame

The grouping of codons during the translation of mRNA into amino acid sequences. During translation the proper reading frame must be maintained. For example, the DNA sequence GCT GGT TGT AAG may be expressed in three reading frames or phases, each of which produces a different amino acid sequence:
GCT GGT TGT AAG—Ala-Gly-Cys-Lys
G CTG GTT GTA AG—Leu-Val-Val
GC TGG TTG TAA G—Trp-Leu-(STOP)

Polypeptide

A linear array of amino acids connected one to another by peptide bonds between the a-amino and carboxy groups of adjacent amino acids. When "polypeptide" is used in this specification, it will be understood by those skilled in the art to include the term "protein."

Genome

The entire DNA of a cell or a virus. It includes, inter alia, the DNA coding for the polypeptides of the cell and operator, promoter, and ribosome binding and interaction sequences, including sequences such as the Shine-Dalgarno sequences for each of those coding sequences.

Gene

A DNA sequence that encodes through its template or messenger RNA ("mRNA") a sequence of amino acids characteristic of a specific polypeptide.

Expression

The process undergone by a gene to produce a polypeptide. It includes transcription of the DNA sequence to a mRNA sequence and translation of the mRNA sequence into a polypeptide.

Plasmid

A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying a gene for tetracycline resistance ($Tet^R$) transforms a cell previously sensitive to tetracycline into one which is resistant to it. A cell transformed by a plasmid is called a "transformant."

Phage or Bacteriophage

A bacterial virus. Many phages consist of DNA sequences encapsulated in protein envelopes or coats ("capsids").

Cloning Vehicle

A plasmid, phage DNA, or other DNA sequence that is able to replicate in a host cell. A cloning vehicle is characterized by one or a small number of endonuclease recognition sites at which such DNA sequences may be cut in a determinable fashion without attendant loss of an essential biological function of the DNA, e.g., replication, production of coat proteins, or loss of promoter or binding sites. A cloning vehicle usually contains a marker suitable for use in the identification of transformed cells, e.g., tetracycline resistance or ampicillin resistance. A cloning vehicle is often called a vector.

Cloning

The process of obtaining a population of organisms or DNA sequences derived from one such organism or sequence by asexual reproduction.

Recombinant DNA Molecule or Hybrid DNA

A molecule, comprising segments of DNA from different genomes joined end-to-end outside of living cells, that may be maintained in living cells.

Expression Control Sequence

A sequence of nucleotides that controls and regulates expression of genes when operatively linked to those genes. They include the lac system, the $\beta$-lactamase system, the trp system, the tac system, the trc systems, the major operator and promoter regions of phage $\lambda$, the control region of fd coat protein, the early and late promoters of SV40, promoters derived from polyoma virus and adenovirus, metallothionine promoters, the promoter for 3-phosphoglycerate kinase or other glycolytic enzymes, the promoters of acid phosphatase, e.g., Pho5, the promoters of the yeast $\alpha$-mating factors, and other sequences known to control the expression of genes of prokaryotic or eukaryotic cells and their viruses or combinations thereof. For mammalian cells the gene can be linked to an eukaryotic promoter such as that for the SV40 early region coupled to the gene encoding dihydrofolate reductase and selectively amplified in Chinese hamster ovary cells to produce a cell line containing many copies of actively transcribed eukaryotic genes.

In one embodiment this invention is directed to recombinant DNA molecules, taken from Corynebacterium sp. SHS 752001, characterized by a DNA sequence that codes for the 2,5-DKG reductase of this invention. In another embodiment, this invention is directed to a host, preferably *Erwinia citreus*, transformed by such a recombinant DNA molecule.

The recombinant DNA molecules of this invention are characterized by a DNA seguence coding for the 2,5-DKG reductase of this invention and an expression control sequence that is operatively linked to that DNA sequence in the recombinant DNA molecule. A wide variety of expression control sequences may be used in the recombinant DNA molecules of this invention. These include the lac system, the $\beta$-lactamase system, the trp system, the tac system, the trc systems, the major operator and promoter regions of phage $\lambda$, the control region of fd coat protein, the early and late promoters of SV40, promoters derived from polyoma virus and adenovirus, metallothionine promoters, the promoter for 3-phosphoglycerate kinase and other glycolytic enzymes, the promoters of acid phosphatase, e.g., Pho5, the promoters of the yeast α-mating factors, neomycin phosphotransferase promoter, and other sequences known to control the expression of genes of prokaryotic or eukaryotic cells and their viruses or combinations thereof. For mammalian cells, the gene can be linked to an eukaryotic promoter such as that for the SV40 early region coupled to the gene encoding dihydrofolate reductase and selectively amplified in Chinese hamster ovary cells to produce a cell line containing many copies of it. The preferred expression control sequence of this invention is derived from the lac sequence of pUC8.

In addition, the recombinant DNA molecules of this invention may comprise DNA sequences from a variety of plasmids and phages that allow them to replicate in the chosen host. Preferably, they also include a selection marker, e.g., a DNA sequence coding for a drug resistance. Such plasmid and phage sequences may be derived from, for example, segments of chromosomal, non-chromosomal, and synthetic DNA sequences, such as various known derivatives of SV40 and known bacterial plasmids, e.g., plasmids from $E.$ $coli$ including col E1, pCR1, pBR322, pMB9 and their derivatives, wider host range plasmids, e.g., RP4, phage DNAs, e.g., the numerous derivative of phage λ, e.g., NM989, and other DNA phages, e.g., M13 and Filamenteous single-stranded DNA phages and vectors derived from combinations of plasmids and phage DNAs, such as plasmids which have been modified to employ phage DNA or other expression control sequences or yeast plasmids such as the 2 μ plasmid or derivatives thereof.

It should of course be understood that not all vectors and expression control sequences will function in the same way to express the modified DNA sequences of this invention and to produce the new 2,5-DKG reductase of the present invention. Neither will all hosts function equally well with the same expression system. One skilled in the art, however, may make a selection among these vectors, expression control sequences, and hosts without undue experimentation and without departing from the scope of this invention. For example, in selecting a vector, the host must be considered because the vector must replicate in it. The vector's copy number, the ability to control that copy number, and the expression of any other proteins encoded by the vector, such as antibiotic markers, should also be considered.

In selecting an expression control sequence, a variety of factors should also be considered. These include, for example, the relative strength of the system, its controllability, and its compatibility with the DNA sequence encoding the 2,5-DKG reductase of the present invention, particularly as regards potential secondary structures.

The DNA sequence for the 2,5-DKG reductase of this invention may be used to produce that reductase in a wide variety of hosts, e.g., bacteria such as strains of $E.$ $coli$, such as $E.$ $coli$ C600, $E.$ $coli$ ED8767, $E.$ $coli$ DH1, $E.$ $coli$ LE392, $E.$ $coli$ HB101 , $E.$ $coli$ X1776, $E.$ $coli$ X2282, $E.$ $coli$ MRCI, and strains of Pseudomonas, Bacillus and Streptomyces, yeasts and other fungi, animal hosts, such as Chinese hamster ovary cells or mouse cells, other animal (including human) hosts, plant cells in culture or other hosts. After expression, the enzyme is then useful for transforming 2,5-DKG to 2-KLG.

Hosts for the DNA sequence of the 2,5-DKG reductase of this invention generally should be selected by consideration of their compatibility with the chosen vector, the toxicity of the 2,5-DKG reductase of the present invention to the host, susceptibility of the desired protein to proteolytic degradation by host cell enzymes, contamination or binding of the 2,5-DKG reductase by host cell proteins difficult to remove during purification, expression characteristics, the ability of the host to produce and secrete the 2,5-DKG reductase, the ability of the host to fold the reductase correctly, the fermentation requirements of the host, the ease of purification of the 2,5-DKG reductase from the host, safety, and cost.

In one embodiment, $Erwinia$ $citreus$ SHS 2003 is selected as a host because it produces 2,5-DKG from glucose, and 2-KLG may be produced directly from glucose by a transformed $Erwinia$ $citreus$ SHS 2003.

Most preferably hosts of the present invention are Erwinia citreus, SHS2003 (Ferm-P No. 5449; ATCC No. 31623) and a strain mutated from $Erwinia$ $citreus$ SHS2003, $Erwinia$ $citreus$ ER1026, that is unable to use either 2,5-DKG or 2-KLG as a sole carbon source.

The following example shows some embodiments of the invention but is not intended to limit the scope of the invention.

EXAMPLE

Identification Of A Polypeptide Sequence of the 2,5-DKG Reductase Of This Invention, and Preparation of Cloning Vectors Corynebacterium sp. SHS752001 was described in T. Sonoyama et al., "Production of 2-keto-L-gulonic acid from D-glucose by two-stage fermentation,"$App.$ $and$ $Envir.$ $Microbiol.,$ 43, 1064–69 (1982). Thus, the disclosed strain of Corynebacterium, selected as the donor of a DNA sequence coding for a 2,5-DKG reductase. To aid in identifying the 2,5-DKG reductase gene from that strain of Corynebacterium, a sample of an enzyme was isolated and purified to 95% purity using the following procedure:

A. Cultivation of Corynebacterium SHS 752001

1. A freeze-dried culture of Corynebacterium sp. SHS 752001 was rehydrated immediately after opening by adding 0.4 ml of 0.9% NaCl (sterilized at 120° C. for 20 minutes) to the contents of a vial containing the freeze-dried culture;

2. The culture was transferred to a test tube containing 8 mls of a solution containing 0.5% glucose, 0.5% yeast extract (Difco), 0.5% peptone (Difco), 0.1% KH$_2$Po$_4$, 0.02% MgSO$_4$.7H$_2$O and 2.0% agar. The solution pH was 7.0, and the solution had been sterilized at 120° C. for 15 min. Forty hours after the addition of the culture at 28° C., the culture was suspended with 0.4 ml of 0.9% NaCl that had been sterilized at 120° C. for 20 min.;

3. Five lots of 0.1 ml of the suspension from step 2 were added to five agar slants containing the same ingredients as the solution of step 2. The cultures were fermented for the same amount of time and under the same conditions as step 2. The cultures were suspended with 5 ml of 0.9% NaCl (sterilized at 120° C. for 20 min.), and 2.5 ml of the suspension was transferred to a each of ten seed flasks containing 500 ml of medium.

4. A solution containing: 1% glucose, 0.5% yeast extract (Difco), 0.5% peptone (Difco), 0.1% NaNO$_3$, 0.1% KH$_2$PO$_4$, and 0.02% MgSO$_4$.7H$_2$O, and having a pH of 7.0 was sterilized at 120° C. for 15 minutes. Sixty ml of the solution were added to a 500 ml flask containing the culture. After 16-18 hours of cultivation at 28° C., the culture content of 10 such 500 ml flasks were transferred to a 30 liter (L) jar fermentor; and 5. Twenty liters of a solution at pH 7.2, containing 1.8% glucose. 2.7% corn steep liquor 0.31% $NONO_3$, 0.06% $KH_2PO_4$, 4.4 ppm $ZnSO_47H_2O$, 0.72 ppm $Mncl_24H_2O$, 0.2 ppm Vitamin $B_1$-HCl, 0.15 ppm Calcium panthothenate, and 0.005% antiform (Adekanol), was added to the 30 liter jar fermentor containing the culture. The fermentor was incubated at 28° C. with agitation at 400 rpm and an air flow rate of 0.5 v.v.m.. The fermentation was stopped when glucose disappeared from the culture (22 h). The final pH was 7.5 and the final OD was 19.2.

B. Preparation of cell extract

About 750 gr of cells were harvested from the 30 liter jar fermentor by centrifugation using a Sharples centrifuge (10,000 G, 10 minutes) The cells were suspended in 0.1 M tris-HCl buffer (pH 7, 2.5 L), washed three times with the same buffer (2.5 L in each case) using a centrifuge, and finally resuspended in 1.6 L of the buffer (OD 150). The cells (as 80 ml of cell suspension) were disrupted by sonication (160 watts for 7 min.). Unbroken cells and debris were removed by centrifugation (15,000 G for 30 min.), and the supernatant (1 L) was pooled.

C. Fractionation by $AmSO_4$

The protein material that precipitated between 40% and 70% saturation was collected by centrifugation, and redissolved in 80 mls of 0.1M tris-HCl buffer at pH 7. The solution was dialyzed against 0.02 M tris-HCl buffer at pH 7 overnight.

D. Ion-Exchange Chromatography

The dialyzed solution (99 ml) was placed on a DEAE-Sepharose CL-6B column (1.6×30 cm) previously equilibrated with 0.02 M tris-HCl buffer (pH7). The column was washed stepwise with 0.02 M tris-HCl buffer containing zero and 0.2 M NaCl (pH 7). The enzyme was eluted with the same buffer containing 0.3 M NaCl (pH 7). The active fractions were pooled and the protein was concentrated by adding $AmSO_4$ up to 70% saturation. The precipitate was collected and dialyzed as in step C.

E. First Affinity Chromatography

The dialyzed solution (37 ml) obtained from step D was placed on an Amicon Matrix Red A column (1.6×19 cm) previously equilibrated with 0.02 M tris-HCl buffer (pH 7). The column was washed stepwise with 0.02M tris-HCl buffer (pH 7) containing 0.3-0.5M NaCl. The enzyme was eluted with the same buffer containing 0.7-1.0M NaCl. The active fractions (90 ml) were pooled.

F. Second Affinity Chromatography 0.02M tris-HCl buffer (pH 7, 225 ml) was added to the pooled fraction from step E, and the resulting solution was placed on an Amicon Matrix Red A column (1.9×12.3 cm) previously equilibrated with 0.02M tris-HCl buffer (pH 7). The column was washed with 0.02M tris-HCl buffer (pH 7) containing 0.2M NaCl. The enzyme was eluted with the same buffer containing 0.5 mM NADPH. The active fractions (35 ml) were pooled and concentrated by ultra-filtration (cut-off below M.W. of 10,000) to remove NADPH.

To demonstrate that the 2,5- DKG reductase of this invention was not denatured during the sonication process and to confirm that the 2,5-DKG reductase of this invention converts 2,5-DKG to 2-KLG, a mixture of 0.1M tris-HCl (pH7) was prepared containing 7 mg NADPH, 2 mg 2,5-DKG and 50 μl cell sonicate at a total protein concentration of 2.5 mg/μl. The total reaction volume was 200 μl. The products of the reaction were analyzed by HPLC, and the presence of 2-KLG was confirmed.

Antibodies to the 2,5-DKG reductase of this invention were prepared. The antibodies were developed by injecting a rabbit intradermally at multiple sites with 100 μg of the 2,5-DKG reductase of this invention in Freunds adjuvant and boosting with 50 μg of the enzyme in Freunds incomplete solution twenty-one days later. Serum was taken ten days after the boost injection and was shown to be positive for anti-(2,5-DKG reductase of this invention) activity in an enzyme-linked immunoabsorbant ("ELISA") assay.

The purified enzyme was sequenced from the N-terminus using a high sensitivity gas phase sequenator manufactured by Applied Biosystems. The partial sequence obtained by this method is shown in FIG. 1. A question mark in the Figure indicates that a particular amino acid could not be determined with absolute certainty.

The purified enzyme was also cleaved using a standard cyanogen bromide clevage procedure. A portion of the amino acid sequence of one 14,000d fragment produced by that method is shown in FIG. 2.

In order to select from a library of clones a DNA sequence coding for that 2,5-DKG reductase of this invention, a series of oligonucleotide probes (shown in FIGS. 3a-e) was prepared, using the phosphotriester method. These probes were derived from the amino acid sequences of FIGS. 1 and 2.

Because of the degeneracy of the genetic code, each probe was actually a family of structurally related molecules. For example, the 14-mer DNA probe of FIG. 3a (Probe I of FIG. 1) had a redundancy of 96 with one C-T mis-match over the predicted sequence, the 14-mer DNA probe of FIG. 3b (Probe II of FIG. 1) had a redundancy of 32 with one G-T mis-match, the 17-mer DNA probes of FIGS. 3c and 3d (Probe III of FIG. 1) each had a redundancy of 32 and differed from one another only in the first two positions, and the 14-mer DNA probe of FIG. 3e (Probe IV of FIG. 2) had a redundancy of 32.

To construct libraries of Corynebacterium DNA to permit screening by the probes of FIGS. 3(a-e) to select the 2,5-DKG reductase gene of this invention, Corynebacterium sp SHS 752001 was lysed by treating a cell suspension of Corynebacterium sp. SHS 752001 with lysozyme (1 mg/l in 10 mM Tris-HCl (pH 8); 1 mM EDTA and 20% (w/v) sucrose followed by sodium dodecylsulfate (SDs) (5 mg/ml). DNA from the lysed Corynebacterium sp. SHS 752001 cells was then fragmented using the restriction endonuclease Sau3a in a buffer comprising 150 mM NaCl, 6 mM Tris-HCl (pH 7.9), 6 mM $MgCl_2$, and 100 μg/ml bovine serum albumin. The DNA fragments were then inserted into pUC8 vectors at a BamHI site using the method of J. Viera and J. R. Messing, Gene, 19, 259 (1982), and the recombinant plasmids were transformed into Escherichia coli JM83, W3110i$^q$, and W3110i$^q$ recA. The method for transformation of the recombinant plasmids into *E. coli* JM83 is set forth in J. R. Messing, R. Corea, P. H. Seeburg, *Nucleic Acids Res.*, 9, 309 (1981). Similar methods were used for other host strains.

Colonies of the resulting library were screened with the probes of FIGS. 3(a–e) using the procedure set forth in Wallace, R. B., Johnson, M. J., Hirose, T., Miyake, T., Kawashima, E. H. and Itakura, K., *Nucleic Acids Res.*, 9, 879–94 (1981). The probes were hybridized at 37° C. and were also washed at 37° C. in a standard wash comprising 6×SSC, 5×Denhardt's buffer, 0.1% SDS, and 0 μg/ml t-RNA. Of seventeen colonies that were positive (hybridized) with the probe of FIG. 3e, two were also positive with the probes of FIGS. 3c or 3d or both. The two recombinant plasmids of those clones were designated pCBR10 and pCBR13. The foreign DNA of each of the two recombinant plasmids was 3.0 kb long.

Properties of Expression Vectors and Transformants According To the Invention

In order to determine the properties of the recombinant plasmids, including production rates of the 2,5-DKG reductase of this invention by the transformed hosts, the two recombinant plasmids and pUC8, a vector not containing the DNA coding for the 2,5-DKG reductase of this invention, were transformed into *E. coli* W3110i$^q$ recA and *Erwinia punctata* by the procedure set forth in Cohen, S. N., Chang, A. C. Y., and Hsu, L., *Proc. Natl. Acad. Sci. U.S.A.*, 69, 2110 (1972)). Vector pUC8, which is related to pBR322, has a strong lac promoter located slightly upstream from a BamH1 site.

Several procedures were examined for releasing the 2,5-DKG reductase of this invention from the transformed cells that produced it so that production rates could be measured. Sonication was found to be best for *E. coli* and Erwinia.

Extracts of *E. punctata* and of *E. coli* carrying pCBR10 and pCBR13 were analyzed by sodium dodecylsulfate-polyacrylamide gel electrophoresis (SDS-PAGE) (Laemmli, U. K. *Nature*, 227, 680–85 (1970)) and by Western blotting (Thomas, P. S., *Proc. Natl. Acad. Sci. U.S.A.*, 77, 5201–05 (1980)) using anti-(2,5-DKG reductase of this invention) antibody, produced above, to determine the amount of 2,5-DKG reductase of this invention produced by the transformants. Extracts of *E. coli* W3110i$^q$ recA (pCBR13) treated with the lac inducer isopropyl β-D-thiogalactopyranoside (IPTG) contained about five times more enzyme than extracts from uninduced cells with the plasmid carrying the gene.

Confirmation that the 2,5-DKG Reductase of this Invention was not Altered During Recombination The 2,5-DKG reductase produced by *E. punctata* and *E. coli* after transformation with pCBR10 and pCBR13 was examined to see if it was the same enzyme isolated from Corynebacterium sp. SHS 752001.

The molecular weight of the protein, labelled by western blotting of extracts of Erwinia (pCBR13), of *E. coli* W3110i$^q$ recA (pCBR13), and of Corynebacterium, was the same as the molecular weight of the purified 2,5-DKG reductase of this invention (i.e., about 29,000d). Based on comparison of the blots for the different cells, it was estimated that 1–2% of the total cell protein of Erwinia (pCBR13) was the 2,5-DKG reductase of this invention.

We have made further constructions using the λP$_L$ promoter, a strong promoter which can be controlled by the λcI repressor protein. Expression of the λP$_L$ promoter can be controlled by changing the temperature from 30° C. to 42° C. in a strain which also carries the λcI$_{857}$ temperature-sensitive repressor. Increased yields of 2-KLG from recombinant strains were obtained using this promoter system.

FIG. 5 shows the physical map of the vector used for making the plasmids expressing 2,5-DKG reductase under the control of the P$_L$ promoter. Plasmid pPLred332 was made by inserting the fragment coding for 2,5-DKG reductase from plasmid pCBR13 into plasmid p210*. The fragment inserted was generated by digestion of pCBR13 with restriction endonucleases EcoRI and HindIII; the two fragments were separated by electrophoresis through low melting agarose. The vector was also digested with EcoRI and HindIII (see FIG. 5) so that the appropriate fragments could be ligated. The resulting plasmid, pPLred332, was transformed into strain W3110 cI$_{ts}$ to form strain EC1083. This strain carries a chromosomal insertion of the lambda temperature-sensitive repressor gene cI857 Plasmid pPLred332, which comprises the vector element derived from 210* and the insert from pCBR13 as shown in FIG. 5, specifies 2,5-DKG reductase which has the same molecular weight, in both *E. coli* and in *Erwinia citreus*, as that specified by pCBR13.

*Erwinia citreus* ER1026 was transformed with pPLred332 to form strain ER1116.

In order to confirm the amino acid and DNA sequence of the 2,5-DKG reductase of this invention, the 3 kb insert of pCBR13 was sequenced by the Maxam and Gilbert technique (*Proc. Natl. Acad. Sci. U.S.A.*, 74, 560 (1977) and Maxam, A. M. and Gilbert, W., *Meth. Enzym.*, 65, 499–560 (1980)) and by Sanger sequencing using plasmid M13 (Sanger, F., Nickelen, S. and Coulsen, A. R., *Proc. Nat'l Acad. Sci. U.S.A.*, 74, 5463–67 (1977)). Examination of the sequence of the 3.0 kb insert revealed a sequence that coded almost exactly for the first sixty amino acids determined for the enzyme itself (as shown in FIG. 1). The 3.0 kb insert also contained a sequence that coded almost exactly for the amino acid sequence of FIG. 2. The end of the reductase gene in the 3.0 kb insert was indicated by a STOP codon. In this way the reductase gene was determined to be 831 nucleotides long (omitting the STOP codon and including ATG, the START codon), and its sequence is shown in FIG. 4.

The DNA sequence coding for the amino acid sequence of the 2,5-DKG reductase of this invention may be compared to the DNA sequence coding for, and the amino acid sequence of, the polypeptide of European Patent Application No. 132,308. FIG. 4 shows both the DNA sequence and amino acid sequence for the 2,5-DKG reductase of this invention. FIG. 4 of European Patent Application No. 132,308 shows the purported DNA sequence and amino acid sequence of that polypeptide. A comparison of the two figures clearly shows that the 2,5-DKG reductase of this invention and its DNA sequence are markedly different from the amino acid sequence and DNA sequence of European Patent Application No. 132,308.

The Michaelis constant (Km) of an enzyme measures the kinetics of that enzyme. The lower the value of the constant, the higher the activity, or velocity, of the enzyme. The Michaelis constant for the 2,5 DKG reported in European Application No. 132,308 is 15.5 mM, and the Michaelis constant for the 2,5-DKG reductase of this invention (using 100 μM NADPH as a cofactor) in 0.1 M Tris-HCl, pH 7.0 at 30° C. is 2.0 mM.

The following procedures illustrate fermentation of glucose to 2-KLG, a Vitamin C precursor, using a genetically modified organism of this invention.

Fermentation of Glucose to 2-KLG Using Transformed Erwinia

*Erwinia citreus* SHS 2003, on deposit with the American Type Culture Collection, Maryland, U.S.A., ATCC No. 31623 and on deposit with the Fermentation Research Institute, Yatabe, Japan, FERM-P No. 5449, normally expresses enzymes for converting glucose to 2,5-DKG. This strain was transformed with pCBR13, which, as described above, contains a gene that codes for the 2,5-DKG reductase of this invention, using the procedure set forth in Cohen, S. N., Chang, A. C. Y., and Hsu, L., *Proc. Nat'l. Acad. Sci.* U.S.A., 69, 2110 (1972). The resulting strain, designated ER817, thus should contain the genes for all the enzymes required for converting glucose to 2-KLG in a single fermentation.

Strain ER817 was inoculated onto a plate of L-broth agar that contained ampicillin (40 μg/ml). The strain had been taken from a stock culture kept in L-broth plus 15% glycerol at −70° C. After the plate had undergone 24 hours incubation at 18° C., 10 ml of a seed medium (glycerol, 5 g/l; corn steep liquor, 27.5 g/l; $KH_2PO_4$, 1 g/l; pH 6.8) in a 250 ml conical flask was inoculated to an absorbance at 650 mm of 0.05 ($A_{650}=0.05$) with strain ER817 taken from the plate.

The resulting seed culture was incubated for 24 hours at 18° C. with rotary shaking. Ten ml of a production medium (corn steep liquor, 30 g/l; $KH_2PO_4$, 1 g/l; NaCl, 1 g/l; $CaCO_3$, 29 g/l; glucose, 10 g/l; pH 6.8) in a 250 ml conical flask was inoculated to $A_{650}=0.2$ with the seed culture and was incubated with rotary shaking at 28° C. for 65 hours.

The culture was then centrifuged and the supernatant was analyzed for the presence of 2-KLG by high performance liquid chromatography (HPLC). Fifty μl samples of the supernatant were analyzed using a Biorad HPX-87H column at 65° C. (0.6 ml/min) in 0.18N $H_2SO_4$. A peak having a retention time of 8.86 min indicates the presence of 2-KLG. The retention times of the other compounds of interest are as follows: 2,5-DKG, 8.46 min; 2-keto-D-gluconic acid (2-KDG), 9.20 min; gluconic acid, 10.0 min; and fucose, 12.1 min.

The various samples of supernatant showed a peak at 8.86 min, indicating the presence of 2-KLG at a concentration of 1 g/l. To confirm that the compound producing a peak at 8.86 min was 2-KLG, a quantity of known 2-KLG (as the sodium salt) was added to a sample of supernatant. That increased only the peak at 8.86 min, thereby providing the confirmation sought. In contrast, when a sample of culture was taken only 18 hours after inoculation (rather than after 65 hours), HPLC analysis of the supernatant contained 2,5-DKG in a concentration of 7 g/l but no detectable 2-KLG.

To confirm further that 2-KLG (and not 2-KDG) was actually being produced in the 65-hour culture, a quantity of known 2-KDG (as the calcium salt) was added to a sample of the supernatant to a concentration of 1 g/l. HPLC analysis of that spiked culture then showed the presence of a new peak at 9.16 min, but essentially no change in the 2-KLG peak at 8.86 min.

Another method of demonstrating the production of 2-KLG by the culture was also used. By converting any 2-KLG produced by the fermentation to ascorbic acid, a reducing agent, the reducing capacity of a fermentation medium containing 2-KLG may be measured, and the amount of 2-KLG present in the solution before its conversion to ascorbic acid may be calculated. To compensate for the presence of reducing agents other than ascorbic acid in a fermentation mixture, a first sample of a fermentation mixture is treated to convert 2-KLG to ascorbic acid and then the total reducing capacity of the sample is determined. A second sample is prepared that, after conversion of the 2-KLG, has had all ascorbic acid eliminated from the medium. The reducing activities of the two samples are then compared, and the difference in activity should indicate the amount of ascorbic acid present in the samples, and hence the 2-KLG present in the fermentation medium.

A sample of supernatant of a fermentation medium was treated to convert any 2-KLG present into Vitamin C. 75 μl of 8N HCl were added to 50 μl of the supernatant and the mixture was incubated for 30 min at 95° C. 120 μl of 5N NaOH were added and the pH was adjusted to 3.75 using 1N sodium acetate.

Ascorbic acid and any other reducing agents in the mixture would reduce the tetrazolium salt MTT [3-(4,5-dimethylthiazolyl-2)-2,5-diphenyltetrazolium bromide] in the presence of the electron carrier PMS [5-methylphenazium methylsulphate] to a formazan. Such treatment was carried out and it indicated the total of all reducing agents (including Vitamin C) in the mixture.

To facilitate specific determination of Vitamin C, a sample of the fermentation mixture before treatment with MTT and PMS was treated with ascorbic acid oxidase and oxygen to destroy any Vitamin C present. Subsequent treatment with MTT and PMS then indicated the amount of reducing agents other than Vitamin C present, and by difference the amount of Vitamin C (and thus of 2-KLG) was determined. In this way the presence of Vitamin C in the mixture and, therefore, the presence of 2-KLG in the supernatant were proven.

Using the procedure for converting 2-KLG to Vitamin C with samples containing known concentrations of 2-KLG allowed preparation of a standard curve. The curve showed that the supernatant obtained from the 65-hour culture of strain ER817 contained 1 g/l of 2-KLG, agreeing with results of the HPLC analyses. 2-KLG was not detected in the supernatant of a similarly produced and treated culture of another strain of Erwinia citreus that lacks pCBR13 (strain SHS2003).

Conversion of glucose to 2-KLG was carried out with the following fermentation procedure using transformed strain ER817. Inoculation was carried out as in Example 1 but incubation in the production medium was for 30 hours instead of for 65 hours and 100 ml of culture were used. The culture supernatant contained 1 g/l of 2-KLG but less than 0.1 g/l of glucose, 2-KDG, 2,5-DKG, or gluconic acid.

One way of obtaining better yields of 2-KLG is to ensure that none of the intermediates produced in the fermentation of glucose to 2-KLG are being consumed in biological reactions that are unrelated to 2-KLG production. Accordingly, a mutant of *Erwinia citreus* (SHS2003) that was unable to use 2,5-DKG or 2-KLG as sole carbon source was isolated following nitrosoguanidine mutagenesis in the procedure described by Miller. Experiments in Molecular Genetics (mold Spring Harbor, 1974), except that the cells were incubated in the presence of nitrosoguanidine at 30° C. After mutagenesis, the cells were incubated for 18 h at 30° C. in M9 medium, that contained glucose (0.2% w/v) or glycerol (0.4% w/v) as described in Miller, Experiments in Molecular Genetics (Cold Spring Harbor, 1974). Samples of the culture were spread onto plates of M9 glucose or M9 glycerol medium and were then replicated onto plates of M9 medium containing 2,5-DKG (0.5% w/v) or 2-KLG (0.2% w/v). Mutants unable to grow on either of these media were purified by restreaking and were tested for their ability to use a variety of substrates as sole carbon sources. Several mutants were obtained that could not use any of 2,5-DKG, 2-KDG or 2-KLG as sole carbon sources. One such mutant was transformed with plasmid pCBR13 to form strain ER1037, which was then tested for its ability to convert glucose to 2-KLG.

A culture of *Erwinia citreus* ER1037 was deposited in the Deutsch Sammlung von Mikroorganismen culture collection. The culture was deposited on July 22, 1985 and is identified as follows: DSM No. 3404.

A culture of strain ER 1037 was grown for 18 h in L-broth and 90 ml of this culture was inoculated into 500 ml of a medium comprising (per liter): $K_2HPO_4$, 4 g; $KH_2PO_4$, 1 g; $NH_4Cl$, 1 g; $CaCl_2$, 0.01 g; $K_2SO_4$, 2.6 g; casamino acids, 10 g; yeast extract, 1.5 g; corn steep liquor, 10 g; D-mannitol, 20 g; and glucose, 10 g. After 20 h growth at pH 6.0 in a 1 liter fermenter (aeration at 0.7 vessel volumes $min^{-1}$ (v.v.m.); agitation at 800 r.p.m.), the concentration of 2-KLG in the growth medium was 6.25 g/liter.

Using *Erwinia citreus* ER1026 transformed with the plasmid pPLred332, a further improvement in yield of 2-KLG can be achieved. The resulting strain, ER1116, is grown as described above. However, instead of terminating the fermentation described in the example after 20 h, the fermentation was extended by the addition of a further 10 g/L of glucose 12 h after inoculation.

Two further additions of 10 g/L of glucose can also be made 36 h and 60 h after the start of the fermentation. A final level of 2-KLG in the fermentation broth was 19.83 g/L representing a conversion from glucose of 49.4%.

It will be apparent to those skilled in the art that various modifications may be made in the invention without departing from its scope or spirit, and our basic construction can be altered to provide other embodiments which utilize the processes and compositions of this invention. Therefore, it will be appreciated that the scope of this invention is to be defined by the claims appended hereto rather than the specific embodiments which have been presented as examples.

We claim:

1. A DNA sequence coding for a 2,5-DKG reductase, said DNA sequence selected from the group consisting of:

(a) a synthetic or isolated DNA sequence of the formula:

CCGAACATCCCCACCATCAGCCTCAACGACGGACGC
    CCCTTCGCCGAGCCTGGGCTCGGCACGTACAACCTG
    CGCGGCGACGAGGGGGTCGCGGCCATGGTCGCCGCG
    ATCGACTCGGGCTACCGCCTGCTCGACACGGCGGTG
    AACTACGAGAACGAGAGCGAGGTCGGCCGAGCGGTG
    CGCGCGAGCAGCGTCGATCGCGACGAGCTCATCGTG
    GCGGCAAGATCCCGGGCCGCCAGCACGGGCGCGCC
    GAGGCGGTCGACAGCATCCGCGGATCGCTCGACCGG
    CTGGGGCTCGACGTGATCGACCTGCAGCTGATCCAC
    TGGCCGAACCCCAGCGTGGGCCGGTGGCTCGACACC
    TGGCGCGGCATGATCGACGCGCGCGAGGCGGGCCTG
    GTCCGCTCGATCGGCGTCTCGAACTTCACCGAGCCG
    ATGCTGAAGACCCTCATCGACGAGACCGGGGTCACA
    CCCGCGGTCAACCAGGTCGAGCTCCACCCGTACTTC
    CCCCAGGCGGCGCTGCGCGCGTTCCACGACGAGCAC
    GGCATCCGCACCGAGAGCTGGAGCCCGCTCGCCCGG
    CGCAGCGAGCTGCTCACCGAGCAGCTGCTGCAGGAG
    CTGGCGGTCGTCTACGGAGTGACGCCGACGCAGGTG
    GTGCTGCGGTGGCACGTGCAGCTCGGCAGCACCCCG
    ATCCCCAAGTCCGCCGACCCCGATCGCCAGCGCGAG
    AACGCCGATGTGTTCGGCTTCGCCCTCACCGCCGAC
    CAGGTCGATGCGATCTCGGGCCTCGAGCGCGGGCGG
    CTCTGGGACGGCGACCCCGACACGCACGAAGAGATG;
    and (b) synthetic or isolated DNA sequences which, as a result of the degeneracy of the genetic code, code for a polypeptide encoded by the foregoing DNA sequence.

2. A process for producing 2-KLG from glucose comprising the steps of:

(a) isolating a mutant of Erwinia unable to use 2,5-DKG as the sole carbon source;
    (b) transforming said mutant with a recombinant DNA molecule Comprising a DNA sequence according to claim 1 operatively linked to a lambda $P_L$ promoter; and
    (c) fermenting said mutant in a medium comprising glucose.

3. The process of claim 2 wherein the pH of the medium is maintained at about pH 6.0.

4. A recombinant DNA molecule comprising a DNA sequence coding for a 2,5-DKG reductase, said DNA sequence selected from the group consisting of:

(a) a DNA sequence of the formula:

CCGAACATCCCCACCATCAGCCTCAACGACGGACGC
    CCCTTCGCCGAGCCTGGGCTCGGCACGTACAACCTG
    CGCGGCGACGAGGGGGTCGCGGCCATGGTCGCCGCG
    ATCGACTCGGGCTACCGCCTGCTCGACACGGCGGTG
    AACTACGAGAACGAGAGCGAGGTCGGCCGAGCGGTG
    CGCGCGAGCAGCGTCGATCGCGACGAGCTCATCGTG
    GCGGCAAGATCCCGGGCCGCCAGCACGGGCGCGCC
    GAGGCGGTCGACAGCATCCGCGGATCGCTCGACCGG
    CTGGGGCTCGACGTGATCGACCTGCAGCTGATCCAC
    TGGCCGAACCCCAGCGTGGGCCGGTGGCTCGACACC
    TGGCGCGGCATGATCGACGCGCGCGAGGCGGGCCTG
    GTCCGCTCGATCGGCGTCTCGAACTTCACCGAGCCG
    ATGCTGAAGACCCTCATCGACGAGACCGGGGTCACA
    CCCGCGGTCAACCAGGTCGAGCTCCACCCGTACTTC
    CCCCAGGCGGCGCTGCGCGCGTTCCACGACGAGCAC
    GGCATCCGCACCGAGAGCTGGAGCCCGCTCGCCCGG
    CGCAGCGAGCTGCTCACCGAGCAGCTGCTGCAGGAG
    CTGGCGGTCGTCTACGGAGTGACGCCGACGCAGGTG
    GTGCTGCGGTGGCACGTGCAGCTCGGCAGCACCCCG
    ATCCCCAAGTCCGCCGACCCCGATCGCCAGCGCGAG
    AACGCCGATGTGTTCGGCTTCGCCCTCACCGCCGAC
    CAGGTCGATGCGATCTCGGGCCTCGAGCGCGGGCGG
    CTCTGGGACGGCGACCCCGACACGCACGAAGAGATG;
    and (b) DNA sequences which, as a result of the degeneracy of the genetic code, code for a polypeptide encoded by the foregoing DNA sequence.

5. The recombinant DNA molecule of claim 4, wherein said DNA sequence is operatively linked to an expression control sequence in the molecule.

6. The recombinant DNA molecule of claim 5, wherein said expression control sequence is selected from the group consisting of the lac system; the β-lactamase system; the trp system; the tac system; the trc system, the major operator and promoter motor regions of phage λ; and the control region of fd coat protein, the early and late promoters of SV40, promoters derived from polyoma virus and adenovirus, metallothiomine promoters, the promoter for 3-phosphoglycerate kinase or other glycolytic enzymes, the promoters of acid phosphatase, e.g., Pho5, the promoters of the yeast α-mating factors; promoters for mammalian cells such as the SV40 early and late promoters, adenovirus late promoter, and other sequences that control the expression of genes of prokaryotic or eukaryotic cells and their viruses and combinations thereof.

7. A transformant comprising a host transformed with at least one recombinant DNA molecule according to claim 5 or 6.

8. The transformant of claim 7, wherein said host makes 2,5-diketo-D-gluconic acid.

9. The transformant of claim 8, wherein said host belongs to the genus Erwinia.

10. The transformant of claim 9, wherein the host is *Erwinia citreus*.

11. The transformant of claim 6, wherein said host is selected from the group consisting of *Erwinia citreus* SHS2003 and *Erwinia citreus* ER1026.

12. A method for producing a 2,5-DKG reductase comprising culturing a host transformed by a recombinant DNA molecule according to claim 4 or 2.

13. The method of claim 12, further comprising the step of isolating said 2,5-DKG reductase.

14. A process for producing 2-KLG from glucose comprising the step of fermenting the transformant of claim 10 in a medium comprising glucose.

15. A process for producing vitamin C, comprising the steps of:
 (a) fermenting the transformant of claim 10 in a medium comprising glucose to produce 2-KLG; and
 (b) converting said 2-KLG to vitamin C.

16. The recombinant DNA molecule of claim 15 wherein said molecule is pCBR13.

* * * * *